(12) United States Patent
Davey et al.

(10) Patent No.: US 6,380,404 B1
(45) Date of Patent: Apr. 30, 2002

(54) PREPARATION OF NORLABDANE OXIDE

(75) Inventors: Paul Nicholas Davey; Chi-Lam Tse, both of Kent (GB)

(73) Assignee: Quest International B.V., Naarden (NL)

(*) Notice: Subject to any disclaimer, the term of this patent is extended or adjusted under 35 U.S.C. 154(b) by 0 days.

(21) Appl. No.: 09/806,835

(22) PCT Filed: Apr. 10, 2000

(86) PCT No.: PCT/GB00/01338

§ 371 Date: May 29, 2001

§ 102(e) Date: May 29, 2001

(87) PCT Pub. No.: WO00/63200

PCT Pub. Date: Oct. 26, 2000

(30) Foreign Application Priority Data

Apr. 16, 1999 (GB) .............................. 99302951

(51) Int. Cl.[7] .............................. C07D 307/92
(52) U.S. Cl. ...................................... 549/458
(58) Field of Search .......................... 549/458

(56) References Cited

U.S. PATENT DOCUMENTS 5,463,089 A 10/1995 Barton et al. ............... 549/458
5,473,085 A 12/1995 Barton et al. ............... 549/458

FOREIGN PATENT DOCUMENTS

EP 0 822 191 2/1998

OTHER PUBLICATIONS

D.H.R. Barton et al. : Tetrahedron Letters, vol. 35, No. 51, 1994, pp. 9505–8, XP002093646, p. 9505, abstract; first paragraph; scheme 1.

D.H.R. Barton et al. : Tetrahedron Letters, vol. 35, No. 32, 1994, pp. 5801–4, XP000864678, p. 5802, Scheme 1.

*Primary Examiner*—Floyd D. Higel
*Assistant Examiner*—Andrea D'Souza
(74) *Attorney, Agent, or Firm*—Morgan, Lewis & Bockius LLP

(57) ABSTRACT

Norlabdane oxide, which is a well known fragrance material having ambergris-type odors, is prepared from 12-acetoxy-norlabdane oxide by a hydrogenation reaction.

12 Claims, No Drawings

PREPARATION OF NORLABDANE OXIDE

This application is the National Phase of International Application PCT/GB00/01338 filed Apr. 10, 2000 which designated the U.S. and that International Application

FIELD OF THE INVENTION

This invention concerns the preparation of (–)-norlabdane oxide, the full chemical name of which is 1,2,3a,4,5,5a,6,7,8,9,9a,9b-dodecahydro-3a,6,6,9a-tetramethylnaphtho-(2,1-b)-furan. For simplicity this material will generally be referred to herein as norlabdane oxide.

BACKGROUND TO THE INVENTION

Norlabdane oxide may be structurally shown by structure (1) as follows:

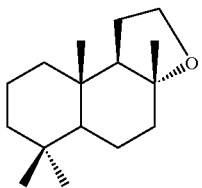

(1)

Norlabdane oxide is a well known fragrance material, which is widely used for providing ambergris-type odours to perfumes. Ambergris is a metabolic product of blue sperm whales which has been used in the past as a valuable constituent of fine fragrances. Natural ambergris itself is no longer used for this purpose. However, there is a demand for perfume ingredients with ambergris-type odours. Norlabdane oxide represents one of the preferred synthetic compounds with desirable ambergris-type odour and is commercially available under various trade names (notably as Amberlyn, Ambroxan, Ambrox or Amberoxide).

A number of synthetic procedures for norlabdane oxide have been published. Many of these procedures use naturally occurring (–)-sclareol, which may be structurally shown by structure (2) as follows:

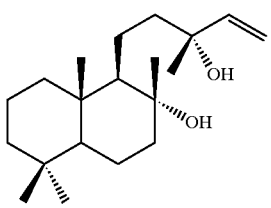

(2)

as the starting material from which norlabdane oxide is obtained in a multi-step synthesis.

U.S. Pat. Nos. 5,463,089 and 5,473,085 describe the conversion of sclareol by use of osmium tetroxide or ozonolysis to an epimeric mixture of methyl-ketone intermediates 12-acetyl-norlabdane oxide which may be structurally shown by structures (3a) and (3b) as follows:

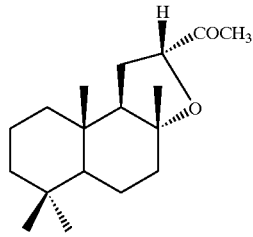

(3a)

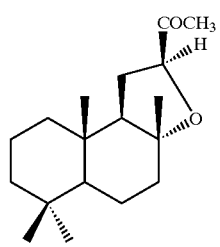

(3b)

Structures (3a) and (3b) may both be represented by structure (3) as follows:

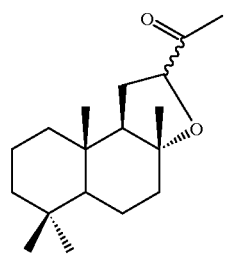

(3)

The 12-acetyl norlabdane oxide of structure (3) is then converted by Baeyer-Villiger oxidation with m-chloroperbenzoic acid in sodium acetate buffer to an epimeric mixture of the acetates 12-acetoxy-norlabdane oxide which may be structurally shown by structures (4a) and (4b) as follows:

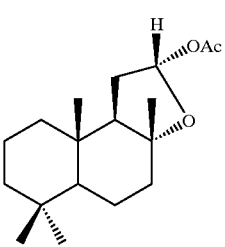

(4a)

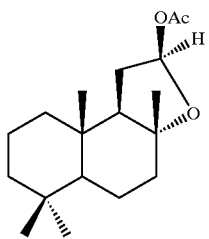

Structures (4a) and (4b) may both be represented by structure (4) as follows:

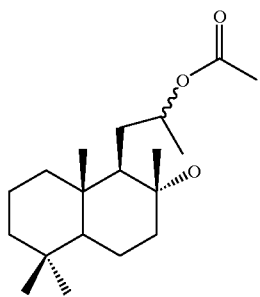

The 12-acetoxy-norlabdane oxide of structure 4 is then reduced to norlabdane oxide of structure (1) by use of LiAlH$_4$/BF$_3$.OEt$_2$.

EP 0822191A describes a generally similar conversion of sclareol to norlabdane oxide, but in which sclareol is converted to 12-acetyl-norlabdane oxide via sclareol oxide. The structure of sclareol oxide may be shown by structure (5) as follows:

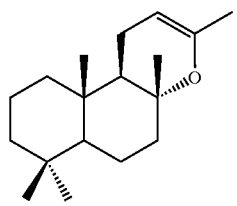

Sclareol is oxidised with ozone, followed by treatment with alkaline hydrogen peroxide to give sclareol oxide. The sclareol oxide is then oxidised with an organic hydroperoxide, preferably tert-butyl hydroperoxide, to give 12-acetyl-norlabdane oxide. The 12-acetyl-norlabdane oxide is converted to 12-acetoxy-norlabdane oxide by oxidation with an organic peracid, preferably peracetic acid. The 12-acetoxy-norlabdane oxide is then reduced to norlabdane oxide with sodium borohydride in the presence of a transition metal salt. The reaction scheme of EP 0882191A may be represented as follows:

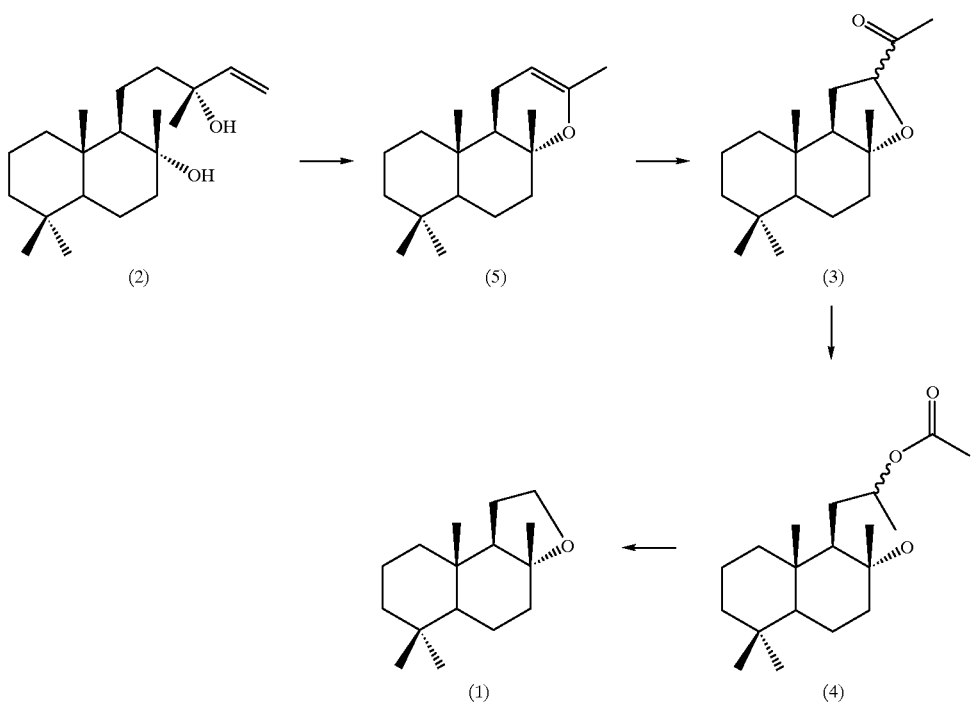

The present invention is based on an alternative, novel approach to conversion of 12-acetoxy-norlabdane oxide to norlabdane oxide in place of the complex metal hydride reduction of the prior art as discussed above.

SUMMARY OF THE INVENTION

According to the invention there is provided a process for preparing (−)-norlabdane oxide from 12-acetoxy-norlabdane oxide, comprising subjecting 12-acetoxy-norlabdane oxide to a hydrogenation reaction to produce (−)-norlabdane oxide.

Compared with the complex metal hydride reduction of 12-acetoxy-norlabdane oxide of the prior art, use of a hydrogenation reaction can have the advantages of reduced effluent and lower cost.

The hydrogenation reaction is conveniently carried out using a hydrogenation catalyst, preferably a noble metal catalyst such as a platinum catalyst. Good results in terms of reactivity and selectivity have been obtained using a platinum/zirconium oxide catalyst, preferably 5% platinum/zirconium oxide catalyst.

The hydrogenation reaction may be carried out in any suitable solvent, particularly inert hydrocarbon solvents such as octane, hexane, decane, cyclohexane, etc, with cyclohexane currently being favoured.

The reaction may be shown as follows:

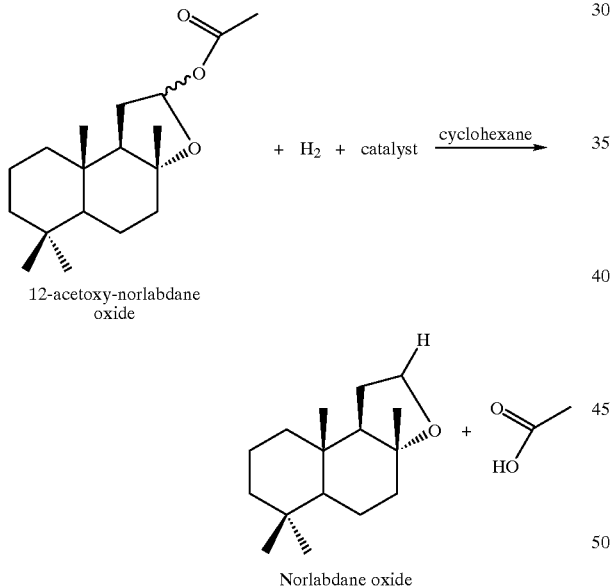

The process of the invention may be carried out using one or both of the epimeric forms of 12-acetoxy-norlabdane oxide, ie pure epimer or an epimeric mixture.

The 12-acetoxy-norlabdane oxide is conveniently prepared as described in EP 0822191A, as discussed above. This involves conversion of sclareol oxide to 12-acetyl-norlabdane oxide by oxidation with an organic hydroperoxide, preferably tert-butyl hydroperoxide, followed by conversion of 12-acetyl-norlabdane oxide to 12-acetoxy-norlabdane oxide by oxidation with an organic peracid, preferably peracetic acid. This process produces the 12-acetoxy-norlabdane oxide in the form of an epimeric mixture, which may be used without requiring purification.

The 12-acetoxy-norlabdane oxide may alternatively be prepared by other known techniques, for example as described in U.S. Pat. Nos. 5,463,089 and 5,473,085.

The invention will be further described, by way of illustration, in the following example.

EXAMPLE 12-acetoxy-norlabdane oxide was prepared as described in EP 0822191A, and the resulting epimeric mixture was used without purification. The 12-acetoxy-norlabdane oxide (2.09 g, 7.10 mmol) was mixed with catalyst in the form of 5% platinum on zirconium oxide (0.2777 g, 0.07 mmol) ex Johnson Matthey, batch 96256, order 56740 in a 50 ml Parr Vessel, and 25 mL of cyclohexane was added. The Parr Vessel was fitted into a Parr Bench Top Microreactor series 4590, and was flushed with nitrogen gas for 2 minutes and then flushed with hydrogen gas. The reactor was then pressurised to 100 bar hydrogen pressure and heated up to 90° C. The hydrogenation was continued at 90° C. at 80–100 bar hydrogen pressure. The reaction was followed by GC and found to be completed in 20.5 hours. The catalyst of the reaction mixture was then filtered and the product was analysed by GC. Norlabdane oxide was identified by NMR and IR spectroscopy as the major product, together with a number of side products identified by GCMS. The structures of the various products are illustrated below, with product distribution in % rpa as identified by GC.

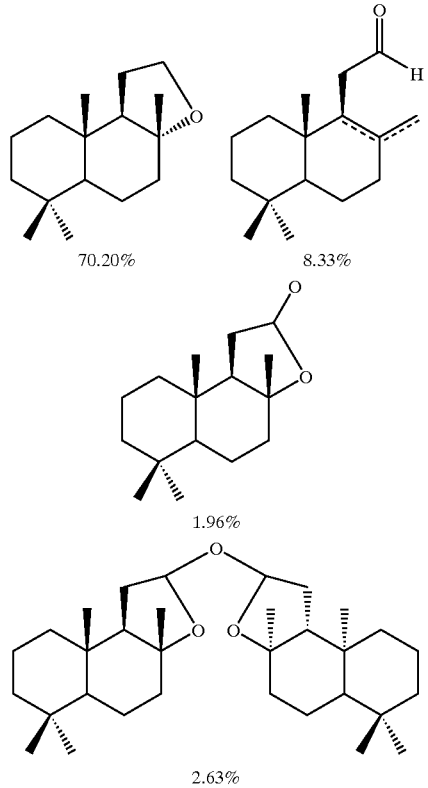

-continued

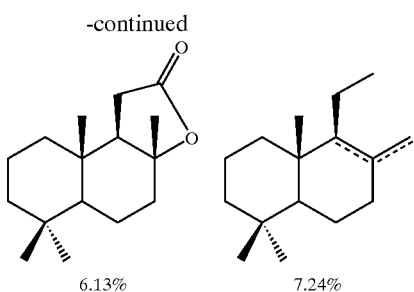

6.13%   7.24%

GC Method
Hewlett Packard HP 6890 GC system
Column: Model. No. HP 19091J-412
  HP-5 5% PhenylMethylsiloxane Capillary
  30.0 mX320 μmX0.25 μm nominal
Temp. Program: 100° C., hold 1 minute, ramp 4° C./min., 280° C., hold 2 minutes
Analytical Methods
NMR: Jeol GSX 400 NMR
Infra-Red Spectroscopy: ATI Mattson Galaxy 5020FTIR Norlabdane oxide may be separated from the mixture by column chromatography for example, for fragrance use.

The best yields of norlabdane oxide have so far been produced using a catalyst of 5% platinum on a zirconium oxide support, as described in the Example above. Experiments using alternative hydrogenation catalysts have shown that reactivity and selectivity can be substantially affected by varying the metal loading of the catalyst, changing the metal and/or changing the support. Platinum catalysts were generally found to be most active and selective. Many of the other catalysts tested were found to be either inactive or not selective in producing norlabdane oxide, producing either no norlabdane oxide or only small amounts of norlabdane oxide together with other reaction products.

What is claimed is:

1. A process for preparing (−)-norlabdane oxide from 12-acetoxy-norlabdane oxide, comprising hydrogenation of 12-acetoxy-norlabdane oxide to produce (−)-norlabdane oxide.

2. A process according to claim 1, wherein the hydrogenation reaction is carried out using a hydrogenation catalyst.

3. A process according to claim 2, wherein the catalyst comprises a noble metal catalyst.

4. A process according to claim 3, wherein the catalyst comprises a platinum catalyst.

5. A process according to claim 4, wherein the catalyst comprises a platinum/zirconium oxide catalyst.

6. A process according to claim 5, wherein the catalyst comprises a 5% platinum/zirconium oxide catalyst.

7. A process according to any one of the preceding claims, wherein the hydrogenation reaction is carried out using an inert hydrocarbon solvent.

8. A process according to claim 7, wherein the hydrogenation reaction is carried out using a solvent selected from octane, hexane, decane and cyclohexane.

9. A process according to claim 8, wherein the hydrogenation reaction is carried out using cyclohexane solvent.

10. A process according to any one of the preceding claims, wherein the 12-acetoxy-norlabdane oxide comprises one or both of the epimeric forms thereof.

11. A process according to any one of the preceding claims, wherein the 12-acetoxy-norlabdane oxide is prepared by oxidation of 12-acetyl-norlabdane oxide with an organic peracid.

12. A process according to claim 11, wherein the 12-acetyl-norlabdane oxide is prepared by oxidation of sclareol oxide with an organic hydroperoxide.

* * * * *